United States Patent [19]

Watanabe et al.

[11] Patent Number: 4,496,931
[45] Date of Patent: Jan. 29, 1985

[54] MOISTURE PERMEABLE ELECTRODE IN A MOISTURE SENSOR

[75] Inventors: Masanori Watanabe, Tenri; Hisatoshi Furubayashi, Yamatokoriyama; Junichi Tanaka, Tenri; Masaya Hijikigawa, Yamatokoriyama, all of Japan

[73] Assignee: Sharp Kabushiki Kaisha, Osaka, Japan

[21] Appl. No.: 590,343

[22] Filed: Mar. 16, 1984

[30] Foreign Application Priority Data

Mar. 23, 1983 [JP] Japan .................................. 58-49150

[51] Int. Cl.³ .......................... H01L 7/00; H01G 5/20
[52] U.S. Cl. ........................................ 338/34; 338/35; 73/335; 73/336.5
[58] Field of Search .................... 338/35, 34; 73/335, 73/336.5, 27 R; 422/98, 97; 427/101, 124, 125, 126.2; 29/620

[56] References Cited

U.S. PATENT DOCUMENTS 2,728,831 12/1955 Pope ..................................... 338/35
3,395,089 7/1968 Mayer et al. .......................... 29/620
4,429,343 1/1984 Freud ................................. 73/336.5
4,442,422 4/1984 Murata et al. ......................... 338/35

FOREIGN PATENT DOCUMENTS 56-009906 1/1981 Japan .
82039004 9/1982 Japan .

OTHER PUBLICATIONS

Halperin et al., "Applying Conductive Coating to a Deformable Polymer", IBM Technical Disclosure Bulletin, vol. 16, No. 7, Dec. 73, p. 2047.

Primary Examiner—Roy N. Envall, Jr.
Assistant Examiner—C. N. Sears
Attorney, Agent, or Firm—Birch, Stewart, Kolasch & Birch

[57] ABSTRACT

A thin-film moisture sensor includes a moisture sensitive polymer film formed on a bottom electrode which is carried on a substrate, and a moisture permeable upper electrode formed on the polymer film. The moisture permeable upper electrode is made of an indium (In) thin-film. In another form, the moisture permeable upper electrode is made of a two-layered electrode including an indium (In) thin-film and a gold (Au) thin-film formed on the indium (In) thin-film.

7 Claims, 4 Drawing Figures

MOISTURE PERMEABLE ELECTRODE IN A MOISTURE SENSOR

BACKGROUND OF THE INVENTION

1. Field of the Invention

The present invention relates to a moisture sensor and, more particularly, to a moisture permeable electrode in a moisture sensor having a moisture sensitive polymer film.

2. Description of the Prior Art

A thin-film moisture sensor has been developed, which includes a moisture sensitive polymer film made of acetate, cellulose, polystyrenesulfonate, polyacrylate, etc. The thin-film moisture sensor detects, for example, the humidity and the dew condensation, and has wide application in, for example, air conditioning apparatus, automobiles, medical care, agriculture, forestry and stockbreeding. The amount of water absorbed in the polymer film increases/decreases in reversible manner depending on the water contents in the atmosphere. This results in a variation of the ionic conductivity or the dielectric constant of the moisture sensitive polymer film. The thus created variation of the dielectric constant or the ionic conductivity is utilized to detect the humidity.

The thin-film moisture sensor generally includes a comb-shaped electrode formed on a substrate, and a moisture sensitive polymer film formed on the comb-shaped electrode. A moisture permeable coating film is disposed on the moisture sensitive polymer film, when required. Instead of the coating film, a moisture permeable conductive film can be formed on the moisture sensitive polymer film, which functions as a counter electrode.

The above-mentioned moisture permeable conductive film must satisfy the following requirements.

(1) The conductive film must show strong adhesion to the moisture sensitive polymer film.

(2) Cracks will not be formed in the conductive film, or the conductive film will not be peeled from the moisture sensitive polymer film even when the polymer film swells or shrinks due to the moisture absorption and the moisture desorption.

(3) The conductive film must show a sufficient moisture permeability.

(4) The conductive film must have a sufficiently low resistance value as compared with the impedance of the moisture sensitive polymer film.

(5) The conductive film should be formed on the moisture sensitive polymer film at a temperature which does not damage the polymer film.

A thin-film moisture sensor has been proposed, which includes a moisture permeable conductive film made of a sintered body such as ruthenium oxide ($RuO_2$), or a metal thin-film such as a gold (Au) film. The sintered body electrode is not suited for the thin-film moisture sensor because the sintered body is formed on the polymer film at a temperature exceeding the thermal resistivity of the moisture sensitive polymer film. The Au thin-film is generally formed on the moisture sensitive polymer film through the use of a vacuum evaporation technique or a sputtering method. However, the substrate temperature can not be set at a considerably high level due to the thermal characteristics of the polymer film. Therefore, the Au thin-film does not show a desirable adhesion to the moisture sensitive polymer film. Furthermore, there is a considerably high possibility that the Au thin-film forms cracks therein or peels from the polymer film when the thin-film moisture sensor is disposed in a high humidity atmosphere and the moisture sensitive polymer film swells.

OBJECTS AND SUMMARY OF THE INVENTION

OBJECTS OF THE INVENTION

Accordingly, an object of the present invention is to provide a novel thin-film moisture sensor which ensures stable operation.

Another object of the present invention is to provide a novel moisture permeable electrode formed on a moisture sensitive polymer film, which ensures stable operation even in a high humidity atmosphere.

Still another object of the present invention is to provide a thin film moisture sensor including a moisture permeable electrode which tightly adheres to a moisture sensitive polymer film.

Other objects and further scope of applicability of the present invention will become apparent from the detailed description give hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

SUMMARY OF THE INVENTION

To achieve the above objects, pursuant to an embodiment of the present invention, a moisture permeable electrode layer made of an indium (In) thin-film is formed on a moisture sensitive polymer film. In a preferred form, a thin-film noble metal layer made of, for example, gold (Au), silver (Ag) or platinum (Pt) is further formed on the indium (In) thin-film in order to ensure stable operation.

The indium (In) thin-film tightly adheres to the moisture sensitive polymer film. The indium (In) thin-film shows a satisfying moisture permeability and electrical conductivity. Furthermore, the indium (In) thin film does not form cracks therein or does not peel from the moisture sensitive polymer film even when the swelling and/or shrinkage occurs in the polymer film.

BRIEF DESCRIPTION OF THE DRAWINGS

The present invention will be better understood from the detailed description given hereinbelow and the accompanying drawings which are given by way of illustration only, and thus are not limitative of the present invention and wherein.

DESCRIPTION OF THE PREFERRED EMBODIMENTS

Figure 1:
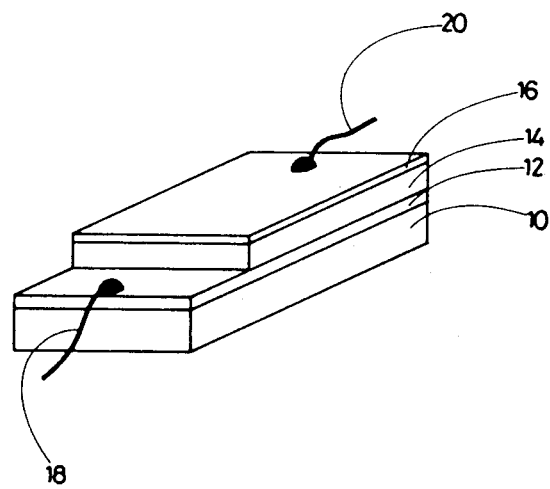
FIG. 1 is a perspective view of an embodiment of a thin-film moisture sensor of the present invention.

A thin-film moisture sensor includes a moisture permeable electrode layer formed on a moisture sensitive polymer film. When the moisture permeable electrode layer is made of a general metal thin-film, there is a great possibility that cracks are formed in the electrode layer and the electrode layer peels from the polymer film due to the swelling and/or shrinkage of the polymer film. To prevent the occurrence of the cracks and the peeling off, the moisture permeable electrode layer must show sufficient ductility and malleability. In the following embodiments, the moisture permeable electrode layer is made of indium (In) which shows desirable ductility and malleability.

More specifically, a thin-film moisture sensor of the present invention includes a substrate 10 made of, for example, glass or ceramics such as sintered alumina having a thickness of about 0.3 mm to 2 mm. A bottom electrode metal layer 12, preferably made of gold (Au), is formed on the substrate 10. A moisture sensitive polymer film 14 is formed on top of the bottom electrode metal layer 12. The moisture sensitive polymer film 14 is preferably made of an organic material, for example, polystyrenesulfonate, polyacrylate, polyvinyl alcohol, a mixture including polyvinyl alcohol and electrolyte such as salt of alginic acid, or a mixture of acetate or cellulose and solvent such as acetone. A moisture permeable upper electrode 16 made of an indium (In) thin-film is formed on the moisture sensitive polymer film 14. A lead wire 18 is connected to the bottom electrode metal layer 12, and another lead wire 20 is connected to the moisture permeable upper electrode 16.

The indium (In) thin-film 16 is formed through the use of a vacuum evaporation technique. The indium (In) thin-film 16 shows a satisfying moisture permeability, and is stable in a harsh environment including the water immersion test and the storage test under high humidity.

In another preferred form, a low resistance metal thin-film made of, for example, gold (Au), silver (Ag) or platinum (Pt) is formed on the indium (In) thin-film 16 in order to stabilize the resistance of the moisture permeable upper electrode 16. The thus formed moisture permeable upper electrode 16 of the two-layered construction shows an extremely low sheet resistivity, below $10\Omega/\square$.

[EXAMPLE I]

A moisture sensitive polymer film (14) was formed by baking polyvinyl alcohol at 180° C. The thus formed polymer film was disposed on a glass substrate (10) which carries a bottom electrode metal layer (12) formed thereon. An indium (In) thin-film (16) was formed on the moisture sensitive polymer film (14) by a vacuum evaporation. The evaporation was conducted in an argon (Ar) environment of $1 \times 10^{-3}$ Torr, and at a deposition rate of 0.5 Å/sec. The thus formed indium (In) thin-film (16) has a thickness of about 400 Å. Then, the lead wires 18 and 20 are connected to the bottom electrode metal layer (12) and the indium (In) thin-film (16), respectively.

For comparison purposes, a similar thin-film moisture sensor was formed, which has a similar substrate, a similar bottom electrode and a similar polymer film to the above-mentioned device, but has an upper electrode made of a gold (Au) thin-film instead of the indium (In) thin-film.

The thus formed two thin-film moisture sensors were observed in the storage test under high humidity. Cracks appeared in the gold (Au) thin-film. However, the indium (In) thin-film was stable. Further, the two thin-film moisture sensors were observed in the water immersion test. The gold (Au) thin-film peeled from the polymer film, but the indium (In) thin-film of the present invention was stable.

[EXAMPLE II]

A moisture sensitive polymer film (14) formed by baking polyvinyl alcohol at 180° C. was disposed on a glass substrate (10) which carries a bottom electrode metal layer (12) formed thereon. An indium (In) thin-film was formed on the moisture sensitive polymer film (14), by a vacuum evaporation, to a thickness of about 100 Å. The evaporation was conducted in an argon (Ar) environment of $1 \times 10^{-3}$ Torr, and at a deposition rate of 0.5 Å/sec. Further, a gold (Au) thin-film was formed on the indium (In) thin-film under the same evaparation condition to a thickness of about 300 Å. That is, the moisture permeable upper electrode (16) has the two-layered construction. Then, the lead wires (18) and (20) were connected to the bottom electrode (12) and the moisture permeable upper electrode (16), respectively. The upper electrode (16) shows a desirable moisture permeability and tight adhesion to the polymer film (14).

Figure 2:
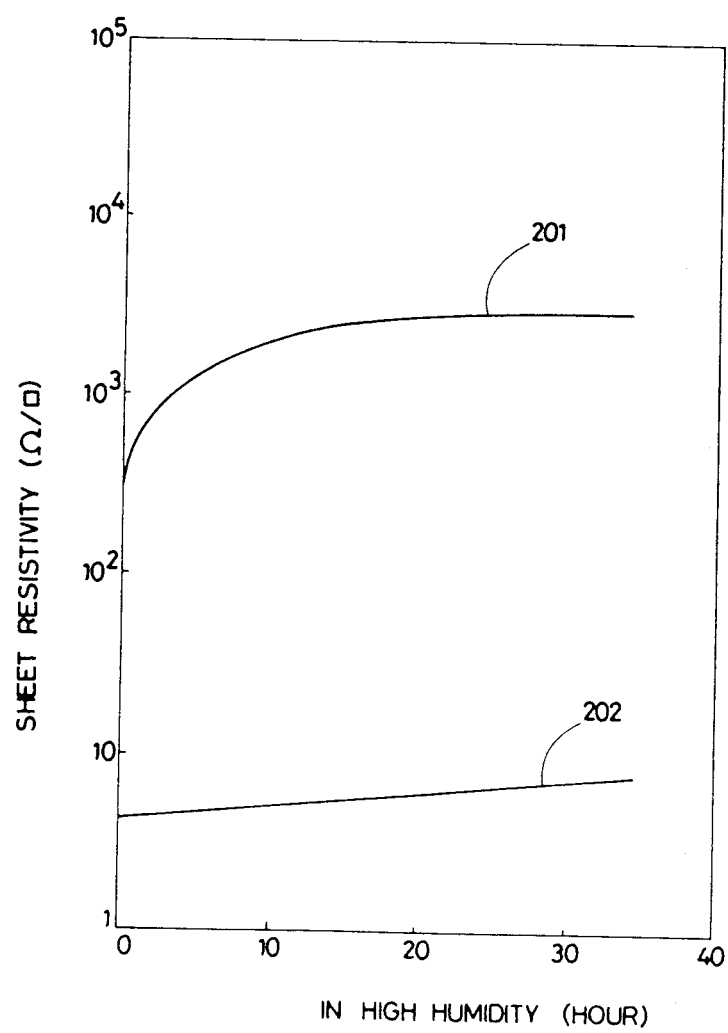
FIG. 2 is a graph showing variations of electrode resistance of the thin-film moisture sensor of FIG. 1 in the storage test under high humidity.

FIG. 2 shows variations of sheet resistivity of the moisture permeable upper electrode (16) in the storage test under high humidity. The curve 201 shows the sheet resistivity of the indium (In) thin-film included in the thin-film moisture sensor of EXAMPLE I. The electrode resistance rises above 1 K$\Omega/\square$ in thirty hours. The curve 202 shows the sheet resistivity of the two-layered upper electrode, including the indium (In) thin-film and the gold (Au) thin-film, of the thin-film moisture sensor of EXAMPLE II. The electrode resistance is stable and less than $10\Omega/\square$ for thirty hours.

Figure 3:
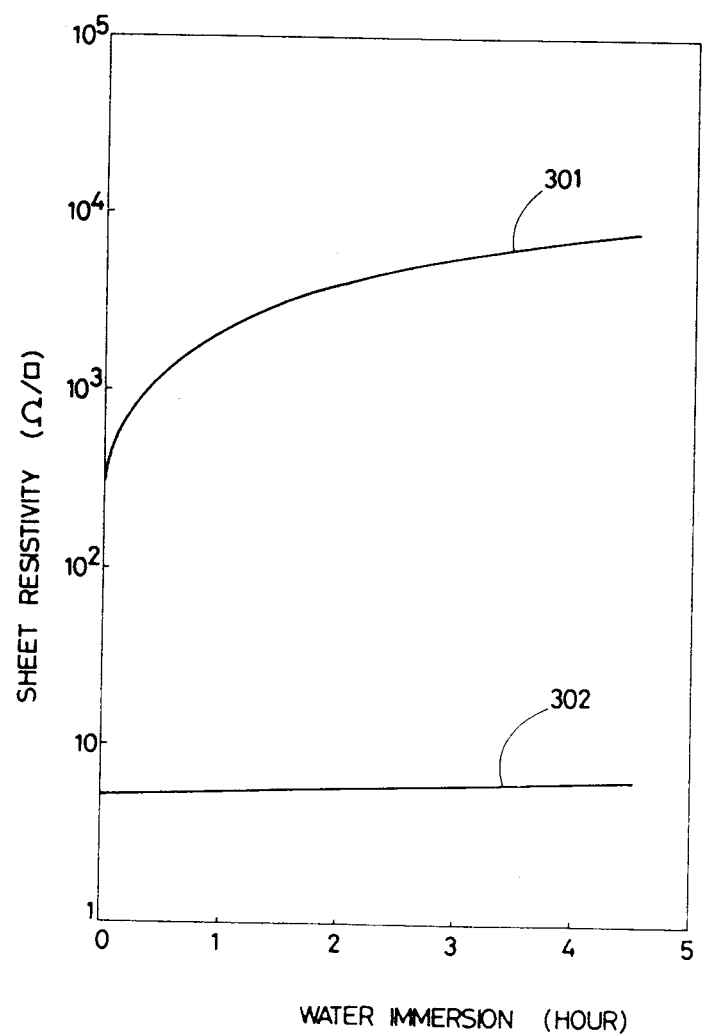
FIG. 3 is a graph showing variations of electrode resistance of the thin-film moisture sensor of FIG. 1 when the water immersion test is conducted.

FIG. 3 shows variations of sheet resistivity of the moisture permeable upper electrode (16) in the water immersion test. The curve 301 represents the sheet resistivity of the indium (In) thin-film included in the thin-film moisture sensor of Example I. The electrode resistance rises above 1 K$\Omega/\square$ in four hours. The curve 302 represents the sheet resistivity of the two-layered upper electrode included in the thin-film moisture sensor of EXAMPLE II. The electrode resistance is stable and less than $10\Omega/\square$ for four hours.

Figure 4:
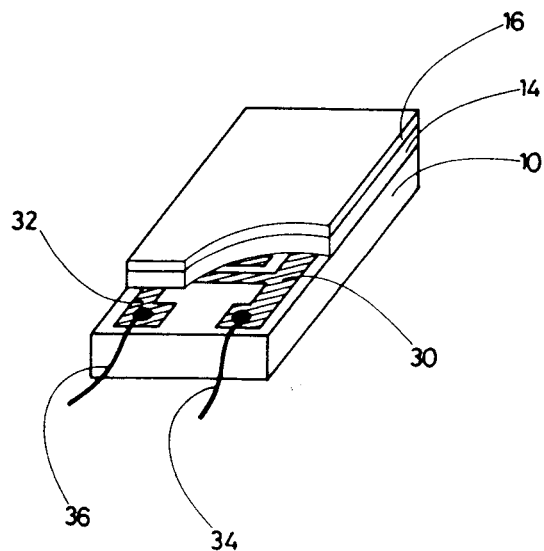
FIG. 4 is a perspective view of another embodiment of a thin-film moisture sensor of the present invention.

FIG. 4 shows another embodiment of a thin-film moisture sensor of the present invention. Like elements corresponding to those of FIG. 1 are indicated by like numerals.

A pair of comb-shaped bottom electrodes 30 and 32 are formed on the substrate 10. The moisture sensitive polymer film 14 is formed on the pair of comb-shaped bottom electrodes 30 and 32, and the moisture permeable indium (In) upper electrode 16 is formed on the moisture sensitive polymer film 14. Lead wires 34 and 36 are connected to the comb-shaped bottom electrodes 30 and 32, respectively. In this embodiment, the moisture permeable indium (In) upper electrode 16 functions as a gate electrode of a field effect transistor (FET) moisture sensor.

The invention being thus described, it will be obvious that the same may be varied in many ways. Such variations are not to be regarded as a departure from the spirit and scope of the invention, and all such modifications are intended to be included within the scope of the following claims.

What is claimed is:

1. A thin-film moisture sensor comprising:
a substrate;

a bottom electrode metal layer formed on said substrate;

a moisture sensitive polymer film formed on said bottom electrode layer; and a moisture permeable indium (In) thin-film formed on said moisture sensitive polymer film.

2. The thin-film moisture sensor of claim 1, wherein said moisture permeable indium (In) thin-film has a thickness of about 400 Å.

3. The thin-film moisture sensor of claim 2, wherein said moisture permeable indium (In) thin-film is formed by a vacuum evaporation.

4. The thin-film moisture sensor of claim 3, wherein said vacuum evaporation is conducted in an argon (Ar) environment of about $1 \times 10^{-3}$ Torr, and at a deposition rate of about 0.5 Å/sec.

5. The thin-film moisture sensor of claim 1, further comprising:

a moisture permeable noble metal thin-film formed on said moisture permeable indium (In) thin-film.

6. The thin-film moisture sensor of claim 5, wherein said moisture permeable indium (In) thin-film has a thickness of about 100 Å, and said moisture permeable noble metal thin-film consists of a gold (Au) thin-film of about 300 Å thick.

7. The thin-film moisture sensor of claim 1, wherein said bottom electrode metal layer comprises a pair of comb-shaped thin-film electrodes.

* * * * *